United States Patent
Pamplin et al.

(10) Patent No.: US 11,406,561 B2
(45) Date of Patent: *Aug. 9, 2022

(54) COMPRESSION GARMENT APPARATUS

(71) Applicant: Koya, Inc., San Francisco, CA (US)

(72) Inventors: John C. Pamplin, Chapel Hill, NC (US); Robert Glenn Dennis, Chapel Hill, NC (US)

(73) Assignee: KOYA, INC., San Francisco, CA (US)

( * ) Notice: Subject to any disclaimer, the term of this patent is extended or adjusted under 35 U.S.C. 154(b) by 673 days.

This patent is subject to a terminal disclaimer.

(21) Appl. No.: 16/409,707

(22) Filed: May 10, 2019

(65) Prior Publication Data

US 2020/0000676 A1    Jan. 2, 2020

Related U.S. Application Data

(63) Continuation of application No. 15/055,400, filed on Feb. 26, 2016, now Pat. No. 10,285,902, which is a (Continued)

(51) Int. Cl.
*A61H 23/02* (2006.01)
*A61H 7/00* (2006.01)
(Continued)

(52) U.S. Cl.
CPC ............ *A61H 23/02* (2013.01); *A61H 7/001* (2013.01); *A61H 7/007* (2013.01); *A61H 11/00* (2013.01); *A61F 13/08* (2013.01); *A61H 2011/005* (2013.01); *A61H 2201/02* (2013.01); *A61H 2201/0207* (2013.01); *A61H 2201/0214* (2013.01); *A61H 2201/5007* (2013.01); *A61H 2205/02* (2013.01); *A61H 2205/04* (2013.01); (Continued)

(58) Field of Classification Search
CPC .............. A61H 7/00–001; A61H 7/007; A61H 11/00–02; A61H 23/00; A61H 23/02–0236; A61H 2209/00; A61H 2201/02; A61H 2201/0207; A61H 2201/0214; A61H 2201/5007; A61H 2205/106; A61H 2205/12; A61F 13/08–085
See application file for complete search history.

(56) References Cited

U.S. PATENT DOCUMENTS 4,018,064 A    4/1977   Doslik
4,527,402 A    7/1985   Swallow et al.
(Continued)

FOREIGN PATENT DOCUMENTS

CN    101098670 B    7/2011
CN    105082129 A    11/2015
(Continued)

*Primary Examiner* — Rachel T Sippel
(74) *Attorney, Agent, or Firm* — Knobbe, Martens, Olson & Bear, LLP

(57) ABSTRACT

A compression garment apparatus for a body part of an human and/or animal having a flexible backing, attaching means, a segmented flex frame, and a shape memory alloy on the segmented flex frame. The shape memory alloy can be connected to two terminals on the frame forming a circuit. A controller can be connected to the terminals applying current to the shape memory alloy at defined intervals providing intermittent, sequenced, or continuous compression therapy.

20 Claims, 9 Drawing Sheets

Related U.S. Application Data continuation of application No. 14/607,249, filed on Jan. 28, 2015, now Pat. No. 9,271,890.

(60) Provisional application No. 61/965,984, filed on Feb. 11, 2014.

(51) Int. Cl.
 *A61H 11/00* (2006.01)
 *A61F 13/08* (2006.01)
(52) U.S. Cl.
 CPC .... *A61H 2205/06* (2013.01); *A61H 2205/106* (2013.01); *A61H 2205/12* (2013.01); *A61H 2209/00* (2013.01); *A61H 2230/065* (2013.01); *A61H 2230/208* (2013.01)

(56) References Cited

U.S. PATENT DOCUMENTS

| | | | |
|---|---|---|---|
| 5,787,732 | A | 8/1998 | Perron et al. |
| 5,996,205 | A | 12/1999 | Mashiko et al. |
| 5,997,465 | A | 12/1999 | Savage et al. |
| 6,123,681 | A | 9/2000 | Brown, III |
| 6,509,094 | B1 | 1/2003 | Shah et al. |
| 7,857,777 | B2 | 12/2010 | Larson et al. |
| 7,868,221 | B2 | 1/2011 | Munch-Fals et al. |
| 7,896,825 | B2 | 3/2011 | Atkinson et al. |
| 8,517,963 | B2 | 8/2013 | Larson et al. |
| 8,523,794 | B2 | 9/2013 | Iker et al. |
| 8,764,689 | B2 | 7/2014 | Toth |
| 9,027,408 | B2 | 5/2015 | Toth |
| 9,161,878 | B1 | 10/2015 | Pamplin et al. |
| 9,248,074 | B2 | 2/2016 | Toth |
| 9,271,890 | B1 | 3/2016 | Pamplin et al. |
| 9,326,911 | B2 | 5/2016 | Wyatt et al. |
| 9,463,821 | B1 | 10/2016 | Critchley et al. |
| 10,071,012 | B2 | 9/2018 | Larson et al. |
| 10,188,152 | B2 | 1/2019 | Stasey et al. |
| 10,285,902 | B2 | 5/2019 | Pamplin et al. |
| 10,426,202 | B2 | 10/2019 | Wyatt et al. |
| 10,441,491 | B2 | 10/2019 | Wyatt et al. |
| 10,617,593 | B2 | 4/2020 | Wyatt et al. |
| 10,668,305 | B2 | 6/2020 | Cheatham, III et al. |
| 10,688,007 | B2 | 6/2020 | Wyatt et al. |
| 10,743,621 | B2 | 9/2020 | Wyatt et al. |
| 2002/0156401 | A1 | 10/2002 | Sherman et al. |
| 2003/0005558 | A1 | 1/2003 | Wong |
| 2005/0043657 | A1 | 2/2005 | Couvillon, Jr. |
| 2010/0234779 | A1 | 9/2010 | Asvadi et al. |
| 2011/0139835 | A1 | 6/2011 | Fikes |
| 2011/0189444 | A1 | 8/2011 | Beers |
| 2012/0065561 | A1 | 3/2012 | Ballas et al. |
| 2012/0101417 | A1 | 4/2012 | Joseph |
| 2012/0232447 | A1 | 9/2012 | Gordon et al. |
| 2013/0030335 | A1 | 1/2013 | Norton |
| 2013/0267995 | A1 | 10/2013 | Voss et al. |
| 2013/0303957 | A1 | 11/2013 | Bauerfeind |
| 2014/0081187 | A1 | 3/2014 | Wyatt et al. |
| 2015/0025426 | A1 | 1/2015 | Larson et al. |
| 2015/0065930 | A1 | 3/2015 | Wyatt |
| 2015/0073318 | A1 | 3/2015 | Holschuh et al. |
| 2015/0073319 | A1 | 3/2015 | Holschuh et al. |
| 2016/0022528 | A1 | 1/2016 | Wyatt et al. |
| 2016/0074234 | A1 | 3/2016 | Abichandani et al. |
| 2016/0120733 | A1 | 5/2016 | Ishikawa et al. |
| 2016/0175179 | A1 | 6/2016 | Pamplin et al. |
| 2016/0193100 | A1 | 7/2016 | Toth |
| 2016/0220808 | A1 | 8/2016 | Hyde et al. |
| 2016/0331620 | A1 | 11/2016 | Kazanchyan et al. |
| 2016/0374886 | A1 | 12/2016 | Wyatt et al. |
| 2017/0196347 | A1 | 7/2017 | Sawhney et al. |
| 2017/0246073 | A1 | 8/2017 | Van-De-Velde |
| 2017/0252252 | A1 | 9/2017 | Wyatt et al. |
| 2017/0304136 | A1 | 10/2017 | Holschuh et al. |
| 2017/0304139 | A1 | 10/2017 | Ross |
| 2017/0312161 | A1 | 11/2017 | Johnson et al. |
| 2018/0055009 | A1 | 3/2018 | Wyatt et al. |
| 2018/0125173 | A1 | 5/2018 | Lambert |
| 2018/0177677 | A1 | 6/2018 | Pamplin et al. |
| 2018/0214616 | A1 | 8/2018 | Muschalek et al. |
| 2018/0242655 | A1 | 8/2018 | Holschuh et al. |
| 2019/0274372 | A1 | 9/2019 | Rizzo et al. |
| 2020/0000677 | A1 | 1/2020 | Pamplin et al. |
| 2020/0154804 | A1 | 5/2020 | Huang |
| 2021/0386614 | A1 | 12/2021 | Doraiswamy et al. |
| 2022/0022606 | A1 | 1/2022 | Doraiswamy et al. |

FOREIGN PATENT DOCUMENTS

| | | |
|---|---|---|
| CN | 105804960 | 7/2016 |
| KR | 10-1569850 | 11/2015 |
| WO | WO 2013/025481 | 2/2013 |
| WO | WO 2013/149985 | 10/2013 |
| WO | WO 2014/172248 | 10/2014 |
| WO | WO 2016/048827 | 3/2016 |
| WO | WO 2016/077150 | 5/2016 |
| WO | WO 2017/027145 | 2/2017 |
| WO | WO 2018/013188 | 1/2018 |
| WO | WO 2018/150372 | 8/2018 |
| WO | WO 2020/144437 | 7/2020 |
| WO | WO 2021/252770 | 12/2021 |
| WO | WO 2022/020370 | 1/2022 |

FIGURE 7B

| USING A SENSOR CONNECTED TO THE SHAPE MEMORY ALLOY OR USING THE SHAPE MEMORY ALLOY ITSELF TO MEASURE AT LEAST ONE PHYSICAL CHARACTERISTIC OF THE COMPRESSION GARMENT APPARATUS INCLUDING CHANGES IN DIMENSION OF THE COMPRESSION GARMENT APPARATUS, STIFFNESS OF THE BODY PART, CHANGES IN DIMENSION OF THE BODY PART, MEASURABLE PHYSIOLOGICAL PARAMETERS OF THE HUMAN AND/OR ANIMAL, SUCH AS HEART RATE AND BLOOD PRESSURE, AND COMBINATIONS THEREOF | 120 |
|---|---|
| CREATING AT LEAST ONE STANDBY PHASE THAT MAINTAINS THE TEMPERATURE OF THE SHAPE MEMORY ALLOY JUST BELOW THE TARGET TRANSITION TEMPERATURE KEEPING THE LENGTH OF THE SHAPE MEMORY ALLOY UNCHANGED BUT PREPARING THE SHAPE MEMORY ALLOY FOR THE SHORTENING OR LENGTHENING OF THE SHAPE MEMORY ALLOY | 122 |
| USING THE CONTROLLER AND COMPUTER INSTRUCTIONS IN THE DATA STORAGE TO COMPARE SENSED REAL TIME MEASURED GARMENT DIMENSIONS TO PRESET GARMENT DIMENSION VALUES AND CHANGE CURRENT DELIVERY TO THE SHAPE MEMORY ALLOY TO ACHIEVE THE PRESET GARMENT VALUES | 124 |

COMPRESSION GARMENT APPARATUS

This application claims the benefit under 35 U.S.C. 120 as a continuation of U.S. application Ser. No. 15/055,400, filed Feb. 26, 2016, which is a continuation of U.S. application Ser. No. 14/607,249, now U.S. Pat. No. 9,271,890, filed Jan. 28, 2015, which claims the benefit of U.S. Provisional Application No. 61/965,984, filed Feb. 11, 2014. Each of the foregoing priority applications are hereby incorporated by reference in their entireties.

BACKGROUND

Field of the Disclosure

The present embodiments generally relate to a compression garment apparatus.

A need exists for a compression garment configured to treat deep vein thrombosis prophylaxis.

A further need exists for a medical aid for the elderly that uses a shape memory alloy.

A need exists for a compression garment that uses a knitted fabric as the flexible backing to aid as a medical device to reducing swelling.

A need exists for a compression garment that provides compression, such as on feet and ankles to reduce swelling.

A need exists for a compression garment usable for treating lymphedema.

The present embodiments meet these needs.

BRIEF DESCRIPTION OF THE DRAWINGS

The detailed description will be better understood in conjunction with the accompanying drawings as follows:

FIGS. 7A-7B is a representation of the steps to build the compression garment apparatus according to the method.

Figure 1:
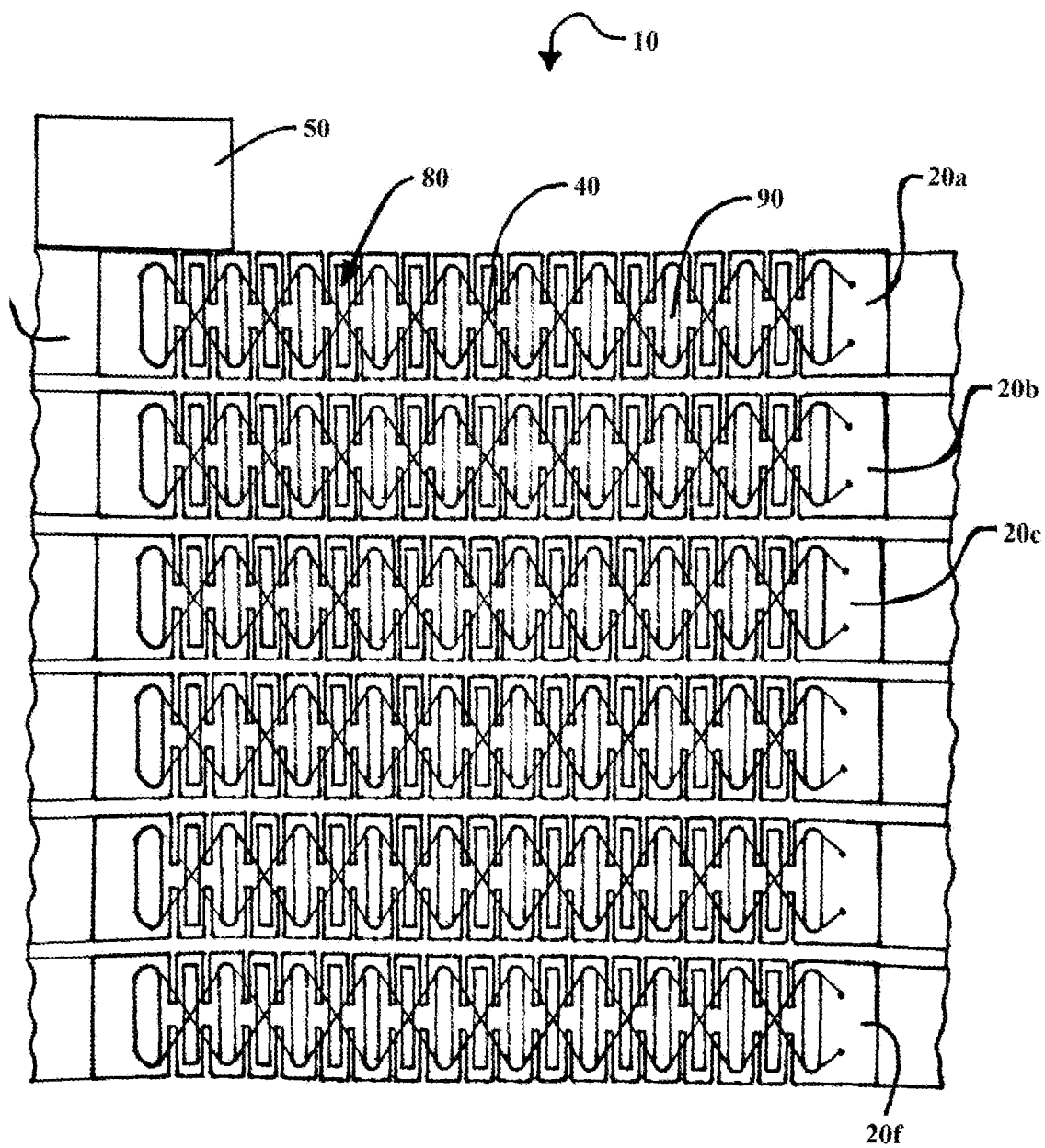
FIG. 1 depicts an embodiment of a compression garment apparatus with a plurality of segmented flex frames.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a compression garment apparatus, such as an active compression sleeve, which is designed to aid circulation of the lower legs by contracting and actively squeezing fluid from the legs back to the thoracic cavity.

The compression can be achieved with the use of shape memory alloy (SMA). The shape memory alloy can be woven into fabric which forms a flexible sleeve that, upon application of current, will compress in a cyclical fashion. This compression propagates up the leg as a wave to encourage fluid flow.

There are two products that are available to consumers on the market currently. The first is a static compression sock and the second is an active sleeve that uses single compartment air bags to compress large areas of the leg simultaneously. The static compression socks are good for mobility and can be worn underneath normal clothing, but do not aid in circulation—they only limit swelling. The second active sleeve requires larger air compression machines, such as those found in hospitals, which aid in circulation, but due to their size and cost, they are not mobile or practical for use in everyday situations.

The compression sleeve is unique due to its use of a smart material to achieve artificial pumping that propagates up the leg more closely resembling natural circulation via the constriction of veins.

With the use of monitoring systems the active compression sleeve can also be programed to compress at different rates and time determined by the user's heart rate.

Another important advantage is the warming up of the shape memory alloy wire through use as heat and pressure are used in conjunction with one another to encourage blood flow. People who would benefit from this include patients with peripheral edema, congestive heart failure, bedridden patients with stagnated fluid flow, patients who suffer from abnormal blood pressure, compartment syndrome, restless leg syndrome, pregnant women, obese patients with poor circulation, people with stationary lifestyles, travelers who spend long periods of time being sedentary, diabetic patients, elderly patients, patients with varicose veins, and/ or any other person suffering from peripheral edema, cramps, or poor circulation.

Note that this technology is not limited to the lower limbs, but can be used in any area suffering from cramps, swelling, or similar problems on any part of the body. The garment and/or sleeve can also be designed to encourage fluid flow to extremities in situations where this would be helpful, specifically after surgery where blood flow may be required to the treated area and those already noted above. Other applications of this technology include massage and muscle relief, sports medicine, and relief from cramps. Smaller bands could provide a more targeted effect for any problem area.

In embodiments, the compression garment apparatus can be in the form of a compression sleeve that can fit over the leg or another body part as needed. The shape memory alloy (SMA) wire ca be incorporated into the fabric (woven, glued, fused are just a few examples) of the compression sleeve in such a way that a change in the lattice structure of the shape memory alloy (SMA) (which occurs through heating) will cause compression of the sleeve.

The incorporation of the shape memory alloy (SMA) wire into the fabric can create a mechanical load that allows distinct compression and relaxation of the compression sleeve. The different wires in the fabric will function independently of each other in order to have a propagating wave. This can be controlled through a control unit, such as a microcontroller.

The shape memory alloy (SMA) requires a certain temperature (as determined by the manufacturing processes) above that of the human body. Examples of shape memory alloy (SMA) can be FLEXINOL™. FLEXINOL™ requires a temperature of 70 degrees Celsius in order to change its lattice structure and thus compress.

Heat treating and cold working the shape memory alloy wire can result in the two distinct lattice structures. To shape the wire initially it must be heated above 70 degrees Celsius to establish its primary shape. When the shape memory alloy wire is then cooled to below the lattice changing temperature, the shape memory alloy (SMA) can be reshaped. Thus when the wire is heated up past the lattice changing temperature, it will revert to its heat treated shape. The temperature that is required to change lattice structure varies. However there are other shape memory alloy formulas that can also be used.

The shape memory alloy wire can be insulated from the human body and the current through the wire will be limited by various fuses. Additionally a quick release mechanism can be incorporated to disconnect power to the compression sleeve and remove the sleeve quickly. The embodiments can include a temperature sensor that can automatically shut off the system if the temperature of the patents skin rises above a specified benchmark.

This temperature increase is achieved through an electrical process such as running current through the shape memory alloy wire (via wall outlet or battery pack) or by some other heating element.

This heat, along with the electricity, can be insulated from the patient through multiple fail-safes in order to ensure safety. The contraction of the compression sleeve will take place in a progressive manner either up or down the leg (or other body part) as needed. This progressive compression and subsequent relaxation can take place in a cyclical manner, the frequency of which can be variable. This technology can also be used in conjunction with other monitoring systems, such as heart rate monitors, pulse oximeters, or similar devices.

The compression sleeve has the ability to provide progressive compression up or down a limb, which allows it to aid in circulation more effectively than a currently available compression sleeve.

In addition, the compression sleeve would be smaller, lighter, sans various wires, and mobile. It is also something that can be worn under clothing while at work, on an airplane, after physical activity or in almost any other situation, which makes it more versatile and adaptable than any existing technologies.

The frequency of compression, direction of progressive compression, positioning, and other features are also variable and thus the sleeve can be customized for a number of different uses and settings.

The product utilizes the best of current high-end technologies and incorporates them into a system that is practical for everyday situations. Its increased mobility and versatility also make it more accessible and helpful in the situations where problems arise, as opposed to patients having to return home or to a particular facility in order to obtain treatment.

With the use of monitoring systems, the active compression sleeve can also be programed to compress at different rates and time determined by the user's heart rate. Another important advantage is the warming up of the shape memory alloy wire through use as heat and pressure are used in conjunction with one another to encourage blood flow.

Parties that can use the compression garment apparatus and/or compression sleeve can include biomedical companies, particularly those that deal in hemostatic imbalances and/or material science, as well as athletic companies, hospitals, rehabilitation centers, nursing homes, and individuals, such as those with peripheral edema or sore legs or other conditions aided by this sleeve.

Sequence of Assembly:

The compression sleeve can be assembled using a fabric that has specific pressure break away points, such as 30 mmHg.

The attachment between the fabric and the shape memory alloy is done in such a way that there is a strong mechanical connection. An example of this attachment can be by using a screw with washers to attach the shape memory alloy and the fabric together.

In embodiments, several different ways to can be used to attach the shape memory alloy and the fabric together, such as a riveted method which that uses a molded plastic piece. The shape memory alloy can be controlled with a microcontroller which has an infinite variability in how the shape memory alloy is activated. The activation can be done with direct current or with a pulse width modulation to vary the speed at which the shape memory alloy contracts.

Sequence of Use:

The patient using the compression sleeve can be fitted or use a standard size depending on the issue that is being addressed. The amount of compression can be controlled by several methods including but not limited to a pressure sensor embedded inside of the sleeve or a patch of fabric acting as a breakaway that can prevent over compression. The compression rating can be designated by the doctor or by standards that are set. The user can then be able to use the sleeve during everyday activity having power either being provided by a power supply, such as a battery pack or by using a constant wall source of power.

A benefit of the invention is that the compression garment apparatus can be worn and the patient or subject can be ambulatory that is the patient can walk around, even run around wearing the apparatus on their body. There is no need for a user to sit still to use the compression device.

A benefit of the invention is that compression garment apparatus can save lives by providing a low-cost, practical medical device for hospital or home use, such as to help treat deep vein thrombosis.

A benefit of the invention is that compression garment apparatus can save lives and can reduce human suffering by providing a way to move and massage arms and legs to help prevent bedsores for patients confined to long-term bed-rest: paralysis patients, coma patients, and the extreme elderly.

A benefit of the invention is that compression garment apparatus can help elderly people by providing warm direct mechanical massage to improve blood flow and retain elasticity of tissues of the arms, legs, hands, feet, and joints.

A benefit of the invention is that compression garment apparatus can help children by providing a device for warm gentle massage for children with blood circulation problems.

A benefit of the invention is that compression garment apparatus can help the handicapped by providing controlled gentle massage in areas that their disability may not allow them to manually access, and for people with amputations.

A benefit of the invention is that dynamic compression garment apparatus can help athletes to recover more quickly from injury and after exercise.

The following terms are used herein.

The term "animal" can refer to humans, dogs, cats, horses, oxen, cows, camels, emus, alligators, and can include canines, and living creatures typically treated by veterinarians.

The term "attaching means" as used herein can refer to a device which is used to connect the flexible backing to the body part and provide tensioning and closing of the apparatus around the body part. Examples of attaching means can include elastic, VELCRO® straps, lacing, or a sleeve of spandex or similar material. In embodiments, the attaching means can be fully flexible and bendable.

The term "body part" as used herein can refer to legs, arms, hands, heads, necks or other body parts of a human or animal needing compression therapy or treatment offered by this invention.

The term "bridge" as used herein can refer to a material that can connect between a spring link and another spring link or between a spring link and a strut, or between a pair of struts. In embodiments, the bridge can be centrally located on each strut or spring link.

In embodiments, the bridges can be aligned along a central axis. Each bridge can connect between a spring link and either (i) another spring link or (ii) a strut forming the segmented flex frame. The bridge can be configured to assist in allowing the spring links to contract at least 1 percent to 75 percent in width of the spring link.

The term "contracted shape" as used herein can refer to a shape wherein the width of the spring link is increased, for example, due to pressure applied by the shape memory alloy.

The term "controller" as used herein can refer to an electronic device with switches, timers and transistors to regulate timing of current applied to the shape memory alloy. In different embodiments, the controller can refer to a microprocessor with data storage and computer instructions in the data storage connected to a power supply. The microprocessor can be used to control timing of current applied to the shape memory alloy.

The term "cooling phase" as used herein can refer to a time period during which a length of the shape memory alloy is cooled to reach a target transition temperature to either lengthen or shorten the shape memory alloy from about 0.25 percent to about 10 percent. The time period can be long or short. In some embodiments the time period can range from 10 minutes and 0.1 seconds, or for example, be a time period such as 3 minutes or 3 seconds. For the cooling phase, the shape memory alloy can either lengthen or shorten, performing a movement that is specifically opposite the movement caused during the heating phase.

The term "data storage" refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals. The data storage is capable of containing computer instructions and instructing the microprocessor to perform various tasks though execution of the computer instructions.

The term "dynamic compression garment" or "compression garment apparatus" as used herein can refer to a wearable article of clothing, such as a knee support, a wrist support or an ace bandage. The term can also include sleeves, socks, long sleeved t-shirt or article of clothing which incorporates the apparatus therein. The term can also include pants, other types of shirts and headgear.

The term "expanded shape" as used herein can refer to a shape wherein the width of the spring link is increased, for example due to pressure applied by a tensioner.

The term "fabric cover" as used herein can refer to a material, which can be a material identical to the flexible backing. The fabric cover can be a woven elastic material or a flexible non-woven material, disposed over the segmented flex frame after the shape memory alloy has been installed on the segmented flex frame. In some embodiments, the fabric cover can have electrical or heating insulation.

The term "fastening strap" as used herein can refer to VELCRO® type fastening straps, elastic straps, or similar straps that are capable of holding the segmented flex frame to the body part.

The terms "first terminal" and "second terminal" as used herein can refer to connections formed on the segmented flex frame which attached to a shape memory alloy. The first and second terminals can both be formed on the same end of the segmented flex frame, or one terminal, such as the first terminal can be formed on one end of the segmented flex frame and the second terminal can be formed on an opposite end of the segmented flex frame. Similarly the terminals can both be formed on one side of the segmented flex frame or a first terminal can be formed on one side and the second terminal can be formed on another side of the segmented flex frame. The terminals can conduct electricity and form an electrical circuit with the shape memory alloy.

The term "flexible backing" as used herein can be used for contacting the body part of the animal and can be a fabric, an expandable non-woven material and can optionally include a liner such as for insulation or water resistance. Usable flexible backings can be made from nylon, polyester, cotton, spandex, parachute material, linen, and any combination of natural and synthetic fabrics.

The term "groove" as used herein can refer to a channel for receiving the shape memory alloy. The groove can be a notch, a cut, a channel, a hole or another type of perforation formed in a strut, for holding the shape memory alloy. In embodiments, the groove can have a depth that is at least 50 percent the diameter or the thickness of the shape memory alloy.

The groove can have an upper groove portion and a lower groove portion with the shape memory alloy extending from one terminal passing alternatingly through upper groove portions of a strut to a lower groove portion of the next sequenced strut, and then the alloy returning from an opposite end of the segmented flex frame alternatingly passing through lower groove portions of the strut that already has the shape memory alloy in the upper groove portions alternating with passing through upper groove portions of struts that already have shape memory alloy in lower groove portions.

The term "heating phase" as used herein can refer to a time period during which a length of the shape memory alloy is warmed to reach a target transition temperature to either lengthen or shorten the shape memory alloy from about 0.25 percent to about 10 percent. The time period can be long or short. In some embodiments the time period can range from 0.1 seconds to 10 minutes, or for example, be a time period such as 3 seconds or 3 minutes.

The term "limb" as used herein can refer to body parts including arms, legs, necks, hands, feet and connecting members, such as the torso.

The term "means for timing" as used herein can refer to either hardware timers or computer instructions in the data storage of the controller to provide current based on preset units of time. The hardware timers can be analog or digital circuitry.

The term "microprocessor" as used herein can refer to a computer, a laptop, a tablet computer, a processor, an integrated processor, embedded microcontroller, or similar device, such as having a size less than ⅕ of an inch that can be attached to a mother board and connected to a power supply. The microprocessor can provide bidirectional communication with a network in embodiments.

The term "network" as used herein can refer to a cellular network, a global communication network, such as the interne, a local area network, a wide area network, a satellite network, a fiber optic network or combinations thereof The term "power supply" as used herein can refer to batteries that supply power which can be mounted to the apparatus, power from a grid or from an alternative energy source which may not be mounted on the apparatus, but are associated with the device such as a fuel cell or solar panel.

The term "preset garment dimension values" as used herein can refer to a set of sizes for the garment which are target expansion and target contraction sizes, such at least one of: a target length and a target width of the segmented flex frame which change over time as the segmented flex frame is dynamically changed in shape.

The term "segmented flex frame" as used herein can refer to a device that connects to the flexible backing and to the attaching means. The segmented flex frame can refer to a plastic or lightweight frame which can have four or more sides. In embodiments the segmented flex frame can be made from a plurality of rectangular, square, oval, or circular segmented components known as "spring links" and/or "struts" connected by bridges.

The term "sensor" as used herein can refer to a device that can be connected to the controller for sensing and generating signals to the controller which can include temperature of the shape memory alloy, metabolic functions of the body part or animal, and expansion and contraction rates of the segmented flex frame.

In embodiments, the shape memory alloy can be used as a sensor to send information to the controller on dimensions of the segmented flex frame and optionally, temperature of the shape memory alloy.

The term "shape memory alloy" as used herein can be nickel or copper alloys including but not limited to: copper-aluminum-nickel alloys and nickel-titanium (NiTi) alloys. Shape memory alloy can also be created by alloying zinc, copper, gold and iron. Although iron-based and copper-based shape memory alloys are usable, so are iron and zinc alloys, including but not limited to Fe—Mn—Si, Cu—Zn—Al and Cu—Al—Ni, or a shape changing non-metal alloy such as a ceramic, a ceramic and glass, a graphite or a composite of these materials, which are non-metal and non-magnetic and which are able to shorten or lengthen when heated to a transition temperature. Shape memory polymer composites are high-performance composites, formulated using fiber or fabric reinforcement and shape memory polymer resin. Representative shape-memory polymers in this category are polyurethanes, polyurethanes with ionic or mesogenic components made by prepolymer method. Other block copolymers also show the shape-memory effect, such as, block copolymer of polyethylene terephthalate (PET) and polyethyleneoxide (PEO), block copolymers containing polystyrene and poly(1,4-butadiene), and an ABA triblock copolymer made from poly(2-methyl-2-oxazoline) and polytetrahydrofuran.

The shape memory alloy can be a linear, amorphous polynorbornene (such as those known as NORSOREX™, developed by CdF Chemie/Nippon Zeon) or organic-inorganic hybrid polymers consisting of polynorbornene units that are partially substituted by polyhedral oligosilsesquioxane (POSS). Crosslinked polyurethanes including those with diisocyanate or those formed using a crosslinker such as glycerin, or trimethylol propane.

Other shape memory alloys can be polyethylene oxide based crosslinked shape memory polymers, such as polyethylene terephthalate (PET) and polyethyleneoxide (PEO), block copolymers. These block copolymers can be the polymers created using maleic anhydride, glycerin or dimethyl 5-isopthalates as a crosslinking agent. The addition of 1.5 weight percent maleic anhydride allows shape recovery of the polymer from 35 percent to 65 percent and provides a tensile strength from 3 to 5 MPa.

Some thermoplastic polymers, most notably polyetheretherketone (PEEK), can be used as well.

The term "spring link" as used herein can refer to a portion of the segmented flex frame which is not rigid and does not receive the shape memory alloy. In some embodiments the spring links can be elliptical or rectangular in shape.

Each spring link can have a center hole to allow the spring link to transition between an expanded shape and a contracted shape.

At least one spring link can connect between a pairs of struts, each spring link can be configured to contract or expand.

Spring links can be made of thermoplastic material or another polymer that is flexible and able to expand and contract in width.

In some embodiments spring links can be made from the identical material as struts and bridges.

The term "standby phase" as used herein can refer to the interval of time when the temperature of the shape memory alloy is held just below a target transition temperature, such as 68 degrees Celsius for a target transition temperature of 72 degrees Celsius.

In the standby phase, a length of the shape memory alloy remains unchanged. In the standby phase, the temperature of the shape memory alloy prepares the shape memory alloy for the shortening or lengthening when additional current is applied to raise the temperature.

The term "strut" as used herein can refer to a portion of the segmented flex frame which has a groove or another holding means, for receiving and holding the shape memory alloy. In some embodiments the strut can have an elliptical or rectangular shape.

Each strut can have a center hole to reduce weight. Struts can be made of thermoplastic material or another polymer that is rigid.

In some embodiments, struts can be made from the identical material as spring links and bridges.

In some embodiments the struts, spring links and bridges can be injection molded as a one piece integral unit.

In some embodiments, each strut and spring link can be configured to have identical lengths and widths.

In some embodiments, the struts and spring links can have a dimension, wherein the width of each strut and spring link is from 20 percent to 90 percent less than the length of each strut and spring link.

Struts, unlike spring links, have a thickness that is at least 10 percent greater than the spring links in order to provide a groove or holding means for the shape memory alloy and provide greater rigidity to the segmented flex frame. The increased rigidity can be an increased resistivity to deformation upon receiving a load onto the segmented flex frame to support the shape memory alloy.

The term "tensioner" as used herein can refer to an elastic material secured to the flexible backing applying a baseline pressure to the body part. A baseline pressure can be just enough pressure to hold the segmented flex frame on the body part without stopping circulation of blood to the body part. The tensioner provides two features simultaneously, first to hold the flexible backing to the body part, and second to pretension the shape memory alloy prior to applying current to the shape memory alloy.

The embodiments further relate to dynamic compression garment for a body part of an animal, such as an arm, leg, foot, hand, neck or other body part.

The compression garment apparatus can have a flexible backing for contacting the body part of the animal, wherein the flexible backing can be a woven stretchable fabric or an expandable non-woven fabric. In embodiments, the flexible backing can include an optional liner for insulation.

The compression garment apparatus can include an attaching means connected to the flexible backing. The attaching means can include elastic bands or buckles on straps.

The compression garment apparatus can include a segmented flex frame connected to the flexible backing and the attaching means.

A first terminal and a second terminal can be formed on the segmented flex frame.

In embodiments, the first and second terminal can both be formed on one end, however, the terminals can be formed on a side of the segmented flex frame or the terminals can be positioned on opposite ends of the segmented flex frame.

In embodiments, the shape memory alloy can be disposed on the segmented flex frame with a first end of the shape memory alloy engaging the first terminal and a second end of the shape memory alloy engaging the second terminal.

The terminals can perform a mechanical connection and an electrical connection simultaneously and the terminals with the shape memory alloy can form a circuit incorporating the shape memory alloy.

A controller with a means for timing can be operatively connected to the first and second terminals.

The controller applies a current to the shape memory alloy at defined intervals using the means for timing thereby providing compression therapy to the body part as the shape memory alloy expands and contracts. In embodiments, hardware timers can be used, including analog timers or digital circuitry.

A power supply can be connected to the controller for providing the current. The power supply can be batteries, or another form of portable power. The power supply provides the current to the shape memory alloy.

The controller executes either an intermittent, sequenced, or continuous compression therapy to the body part.

The compression therapy can include the controller creating at least one heating phase causing a length of the shape memory alloy to reach a target transition temperature to either lengthen or shorten the shape memory alloy from about 0.25 percent to about 10 percent.

The compression therapy can include the controller creating at least one cooling phase causing the length of the shape memory alloy at the target transition temperature to lengthen or shorten opposite of the length change caused by the at least one heating phase.

In embodiments, the fabric backing can include a fabric cover disposed over each segmented flex frame with attached shape memory alloy.

In embodiments, the attaching means can be a tube of expandable fabric or a plurality of fastening straps, such as a plurality of VELCRO® straps or a plurality of elastic straps.

In embodiments, a tensioner can be secured to the flexible backing for applying a baseline pressure to the body part.

In embodiments, the shape memory alloy can be in the form of at least one of: a ribbon, a wire, a mesh, a sheet and a film.

In embodiments, the compression garment apparatus can be formed from a plurality of connected segmented flex frames.

In embodiments, each segmented flex frame can have a plurality of struts. Each of the plurality of struts can have a groove for receiving the shape memory alloy. The groove can be a notch, a cut, a channel, a hole, or another type of perforation. Each segmented flex frame can have a plurality of spring links.

Spring links can be configured to transition between an expanded shape and a contracted shape. At least one spring link can be connected between a pairs of struts.

In embodiments, the spring links can alternate with struts.

Each segmented flex frame can have a plurality of bridges. Each bridge can be centrally located on a strut or spring link, or in a line. Each bridge can connect between the spring link and either (i) another spring link or (ii) the strut.

Each segmented flex frame can be adapted to contract the individual spring links at least 1 percent to 10 percent in width to a contracted shape when the shape memory alloy contracts. The overall length of the segmented flex frame can contract up to 30 percent.

Each segmented flex frame can be configured to expand the individual spring links at least 1 percent to 10 percent in width from the contracted shape to an expanded shape when the shape memory alloy relaxes.

In embodiments, the shape memory alloy can be disposed on the segmented flex frame on alternating components of the segmented flex frame.

The shape memory alloy can be formed on alternative components of the segmented flex frame in either an X-shaped pattern, a sinusoidal pattern, a modified X-pattern, a plurality of circles pattern, or any various pattern usable with the application.

In embodiments, the controller can have a microprocessor, which can be powered by the power supply.

The microprocessor can be in communication with a data storage. The data storage can include computer instructions to instruct the microprocessor to provide preset levels of current to create the compression therapy, such 1 ampere.

The data storage can include computer instructions to instruct the microprocessor to provide current to create the compression therapy, based on preset units of time, such 6 seconds.

In embodiments, the shape memory alloy can act as a sensor to measure at least one physical characteristic of the compression garment apparatus including changes in dimension of the dynamic compression garment, stiffness of the body part and combinations thereof.

The compression garment apparatus can include a sensor connected to the controller for sensing and generating signals to the controller representing at least one of: changes in dimension of the dynamic compression garment, stiffness of the body part; changes in dimension of the body part, measurable physiological parameters of the animal such as heart rate, blood pressure and temperature, and combinations thereof.

The compression garment apparatus can utilize a series of timers. The series of timers can be connected in series. Each timer can provide current to one of the circuits when the timer is "on" and no current when the timer is "off". Each timer can provide current to a portion of the shape memory alloy on at least a portion of a segmented flex frame. Each timer, in embodiments, can operate independent from one another.

In an alternative embodiment, the series of timers can operate sequentially.

The dynamic compression garment apparatus can utilize current that is direct current (DC) or alternating current (AC). The current can be from 3 volts to 48 volts.

It should be noted that the at least one heating phase raises the temperature of the shape memory alloy to a target transition temperature from 40 degrees Centigrade to 110 degrees Centigrade to shorten or lengthen the length of the shape memory alloy.

Additionally in certain uses, the shortening or lengthening of the shape memory alloy can occur within 10 degrees Centigrade of a target transition temperature In embodiments, the controller can create at least one standby phase, wherein the temperature of the shape memory alloy is held just below the target transition temperature keeping the length of the shape memory alloy unchanged but preparing the shape memory alloy for the shortening or lengthening of the shape memory alloy.

In embodiments, the controller can use computer instructions in the data storage to instruct the microprocessor to compare measured garment dimension to a stored preset garment dimension values and change current delivery to the shape memory alloy to achieve the stored preset garment dimension value.

Turning now to the Figures, FIG. 1 depicts an embodiment of the compression garment apparatus 10 with a plurality of segmented flex frames 20a, 20b, 20c, and 20d.

A shape memory alloy 40 is shown and positioned in an X-pattern 80 disposed on each segmented flex frames of the plurality of segmented flex frames.

Each of the segmented flex frames can be connected to a flexible backing 13. In other embodiments, the flexible backing can be segmented and made from a closed cell thin foam material connected at a right angle to the plurality of segmented flex frames.

A controller 50 can be used to provide current to the shape memory alloy 40 disposed on the plurality of segmented flex frames 20a-20d on the flexible backing 13.

Additionally, a sensor 90 is shown positioned over a spring link of the segmented flex frame and connected to the controller 50 which provides timing of power as well as the power to the shape memory alloy 40.

Figure 2:
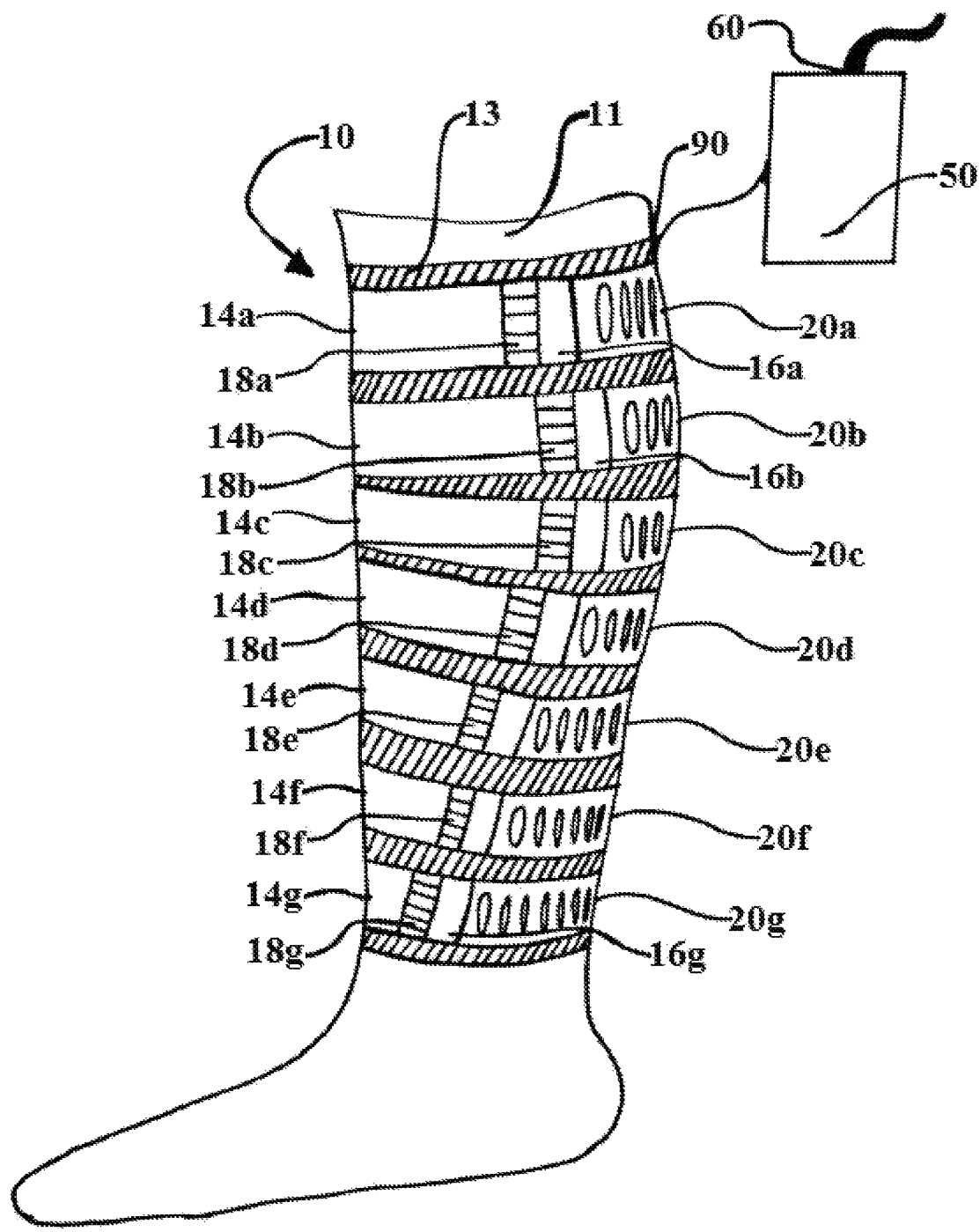
FIG. 2 depicts an embodiment of the compression garment apparatus on a body part of a human.

FIG. 2 depicts an embodiment of the compression garment apparatus 10 constructed on a body part 11, namely a leg of a human.

The compression garment apparatus 10 can have a plurality of attaching means 16a, 16b and 16g connected to the flexible backing 13, which in this embodiment is a very thin, less than 1/16 of an inch thick neoprene.

The compression garment apparatus 10 is shown with a plurality of fabric covers 14a, 14b, 14c, 14d, 14e, 14f, and 14g. Each fabric cover can be installed over a side of each of the segmented flex frames 20a, 20b, 20c, 20d, 20e, 20f, and 20g having the attached shape memory alloy.

A plurality of tensioners 18a, 18b, 18c, 18d, 18e, 18f, and 18g are depicted. The tensioners in this embodiment serve two functions simultaneously, that of tensioning the shape memory alloy and assisting in holding the flexible backing to the body part.

The controller 50 used to provide current to the shape metal alloy disposed on the plurality of segmented flex frames on the flexible backing 13 is shown.

Additionally, a sensor 90 is shown positioned over a spring link of the segmented flex frame and connected to the controller 50 which provides timing of power as well as the power simultaneously to the shape metal alloy.

A power supply 60 is depicted external to the controller 50 in this embodiment enabling the controller 50 to apply current to the shape memory alloy in the segmented flex frames beneath the fabric covers.

Figure 3A:
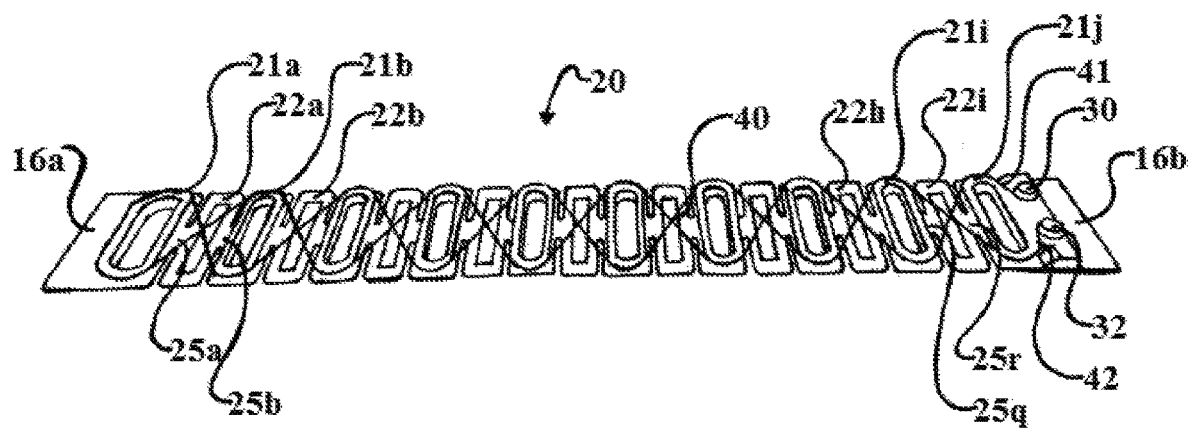
FIG. 3A is a detailed view of a segmented flex frame.

FIG. 3A shows a first attaching means 16a of the segmented flex frame 20.

The first attaching means 16a can be a flat portion integral with and extending from a first strut 21a. The first attaching means 16a can be formed from the same material used to form the rest of the segmented flex frame.

In this embodiment, the first strut 21a has an inverted "D" shape, and additional struts 21b to 21i, each have a rectangular center hole and a generally rounded rectangular shape. The last strut 21j has a generally rectangular center hole integrally formed with a second attaching means 16b.

The second attaching means 16b additionally supports a first terminal 30 and a second terminal 32, which are attached to the second attaching means.

A first end 41 of the shape memory alloy 40 is shown attached to the first terminal 30 and a second end 42 of the shape memory alloy 40 is shown attached to the second terminal 32.

The shape memory alloy 40 is depicted extending from the first terminal 30 entering an upper portion of a groove in the last strut 21j and crossing over a last spring link 22i to enter a lower portion of a groove in additional strut 21i.

A first bridge 25a is shown formed between the first strut 21a and a first spring link 22a. A second bridge 25b is shown connected between the first spring link 22a and additional strut 21b. The third spring link 22b is shown connected to the second strut by a bridge. The spring link 22i is shown connected to the last strut 21j by bridge 25r. Spring link 22i is connected to strut 21i by bridge 25q. The pattern of bridged between components is then repeated.

In this Figure, the spring links are positioned to alternate with the struts. The struts are depicted connected to the spring link by bridges.

In this embodiment, the bridges 25a-25r can all be centrally formed connecting each strut and each spring link at a central location. In this embodiment, the bridges can be small connectors between the larger strut and spring link components.

The shape memory alloy from the first terminal is shown engaging a groove strut 21j, crossing over a spring link 22i to engage another groove in another strut 21i.

In this embodiment, the shape memory alloy is moved from one end, a top of one strut across the spring link to the bottom of another strut. However, it is contemplated that other patterns can be used if attaching means are used which substitute for the grooves.

In embodiments, the shape memory alloy 40 continues down the segmented flex frame to the first strut 21a, wraps through the groove of the first strut 21a and then crosses over the first spring link 22a forming an "x" pattern over the first spring link, and then engaging the additional strut 21b, crossing over the second spring link 22b, and continuing to engage additional struts, again alternating from top to bottom of the struts, opposite the shape memory alloy already positioned on the struts until the shape memory alloy reaches and is connected to the second terminal 32 at the second end 42 of the shape memory alloy.

Figure 3B:
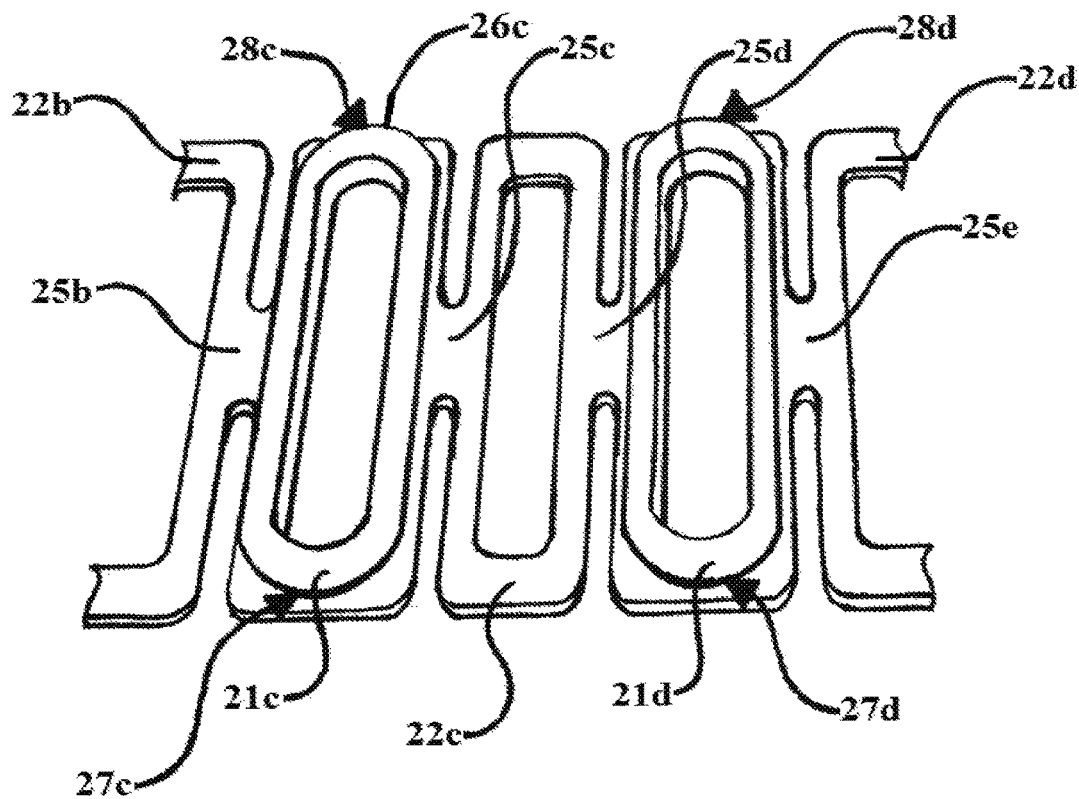
FIG. 3B is a detailed view of a spring link of the segmented flex frame.

FIG. 3B shows the second bridge 25b connecting a second spring link 22b to a third strut 21c.

The third strut 21c can have an upper groove portion 28c and a lower groove portion 27c. In this embodiment, a groove 26c can have both the upper groove portion 28c and the lower groove portion 27c.

The third strut 21c is shown connected to a third spring link 22c and the third spring link engages a fourth strut 21d.

A third bridge 25c, a fourth bridge 25d and a fifth bridge 25e are also shown, as well as fourth strut 21d having an upper groove portion 28d and a lower groove portion 27d and the fourth spring link 22d.

The grooves of the segmented flex frame can be formed in the shape of a complete ellipsoid in the strut. However, in other embodiments, the grooves can be segmented or entirely replaced with different fastening or holding means, so long as the shape memory alloy is connected on opposite ends of the strut and spring links.

Figure 4:
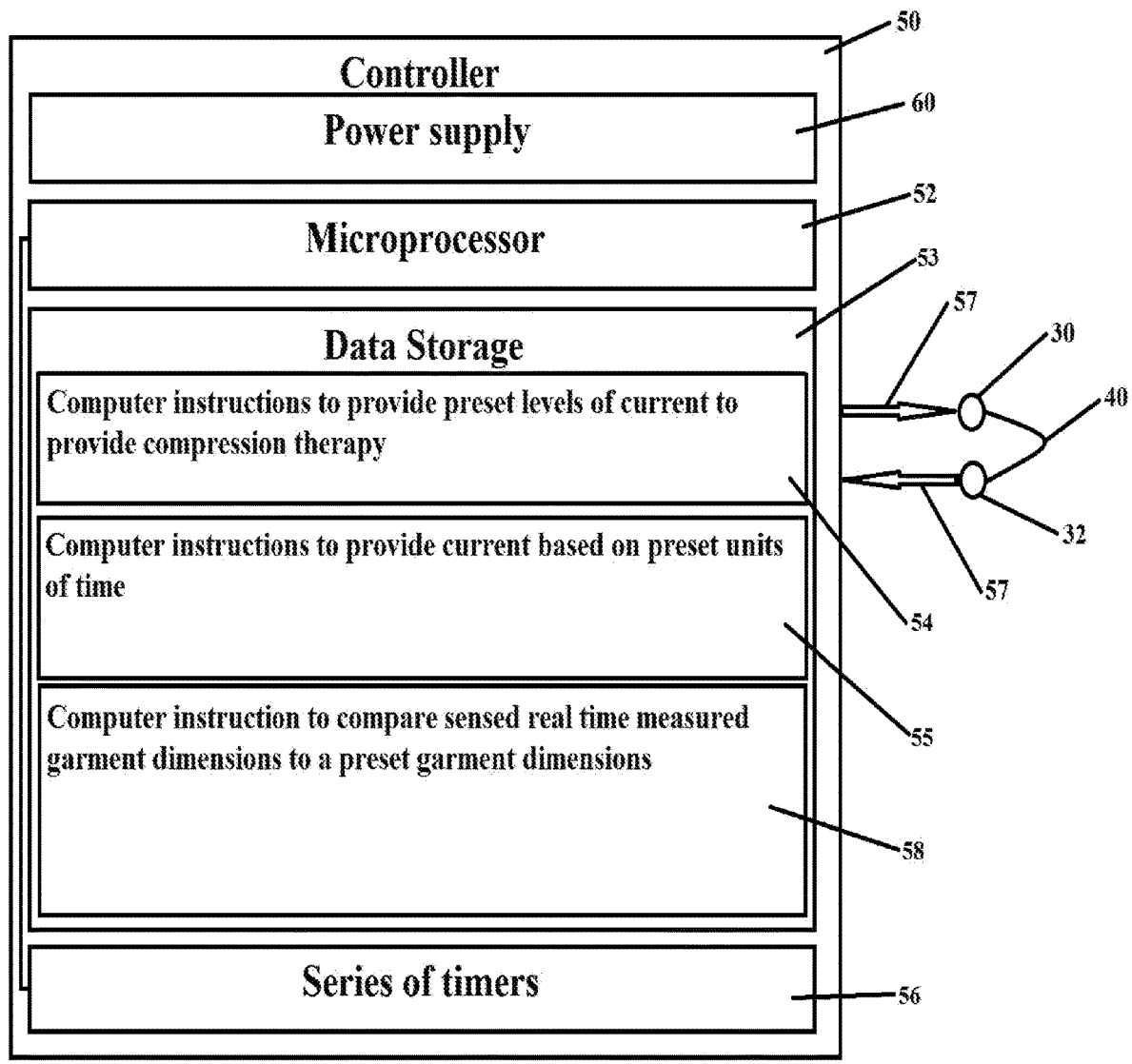
FIG. 4 is a diagram of the controller showing the shape memory alloy forming a circuit.

FIG. 4 is a diagram of the controller showing the shape memory alloy forming a circuit.

The controller 50 is shown containing a microprocessor 52 and a power supply 60 connected to a data storage 53.

In embodiments, the data storage can contain a plurality of computer instructions to instruct the microprocessor to do various tasks.

The data storage 53 can contain computer instructions 54 to provide preset levels for current to provide the compression therapy.

In embodiments, the preset levels for current can be 1 ampere.

The data storage 53 can contain computer instructions 55 to provide current based on preset units of time.

In embodiments, the preset units of time can be 6 seconds.

The data storage 53 can contain computer instructions 58 to compare sensed real time measured garment dimensions to a preset garment dimension values and change current delivery to the shape memory alloy to achieve the preset garment dimension value.

The controller 50 can contain a series of timers 56, wherein each of the timers can be connected in series. In embodiments, each timer can be used to provide current to one of the circuits when the timer is "on" and no current when the timer is "off". In embodiments, each timer can provide current to a portion of the shape memory alloy on at least a portion of a segmented flex frame. In embodiments, each timer can operate independently from one another.

The series of timers can be used in place of computer instructions 55 to provide current based on preset units of time The controller provides current 57 from the power supply at timed intervals to the first terminal 30 through the shape memory alloy 40 to the second terminal 32 forming a circuit.

Figure 5A:
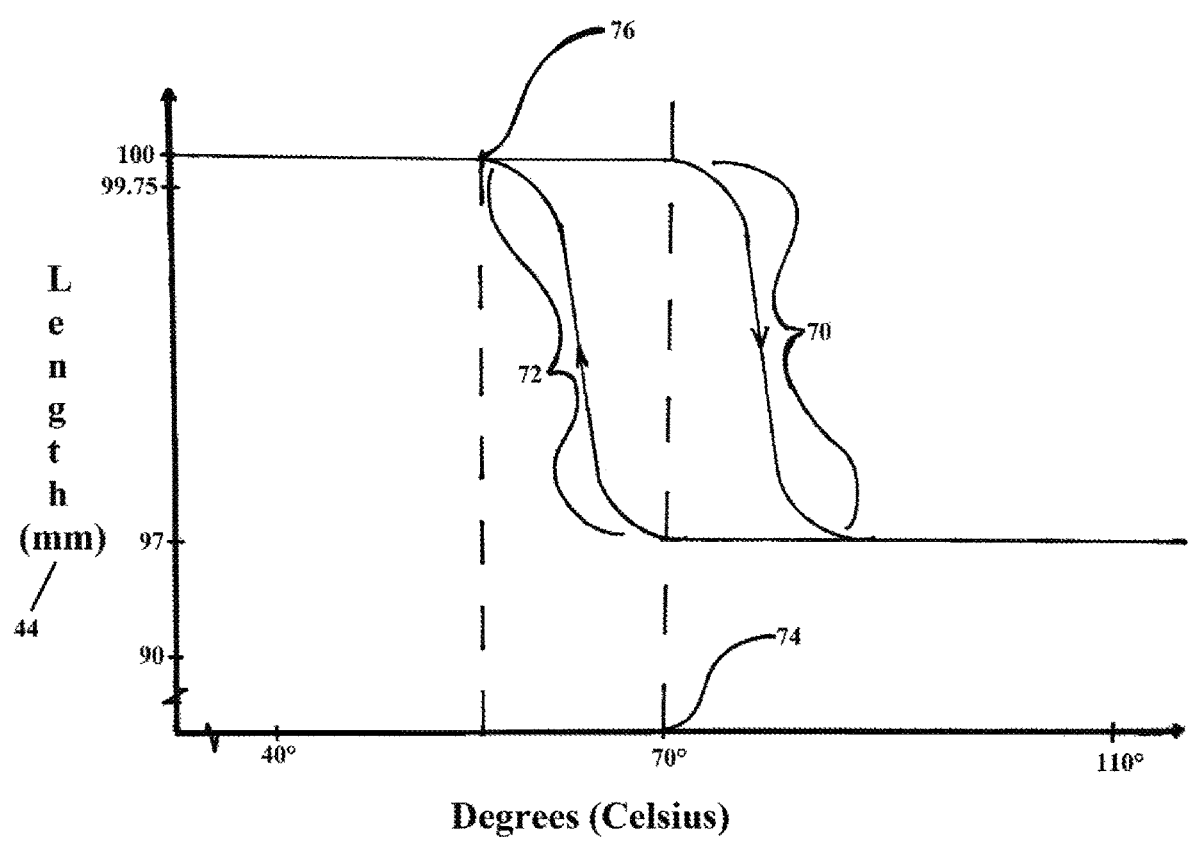
FIG. 5A depicts the heating, cooling and standby phases used by the dynamic compression garment.

FIG. 5A depicts the heating, cooling and standby phases used by the compression garment apparatus.

The graph has an x-axis representing temperatures, wherein one of the temperatures is a target transition temperature 74 of a certain length of shape memory alloy. In this Figure the target transition temperature 74 is shown as 70 degrees Celsius along the x-axis ranging from 40 degrees Celsius to 110 degrees Celsius.

The graph has a y-axis representing the length of the shape memory alloy, here the y-axis is drawn depicting a range from 90 mm to 100 mm with the length of the shape memory allow varying from 97 mm to 100 mm.

The graph shows a heating phase 70 causing a length 44 of the shape memory alloy upon reaching the target transition temperature 74 to either lengthen or shorten. Typically, the shape memory alloy either lengthens or shortens by about 0.25 percent to about 10 percent.

The graph shows a cooling phase 72 which causes a length 44 of the shape memory alloy at the target transition temperature 74 to either lengthen or shorten opposite to the length change caused by the heating phase.

The graph shows a standby phase 76 that maintains the temperature of the shape memory alloy just below the target transition temperature 74 keeping the length 44 of the shape memory alloy unchanged but preparing the shape memory alloy for the shortening or lengthening of the shape memory alloy.

Figure 5B:
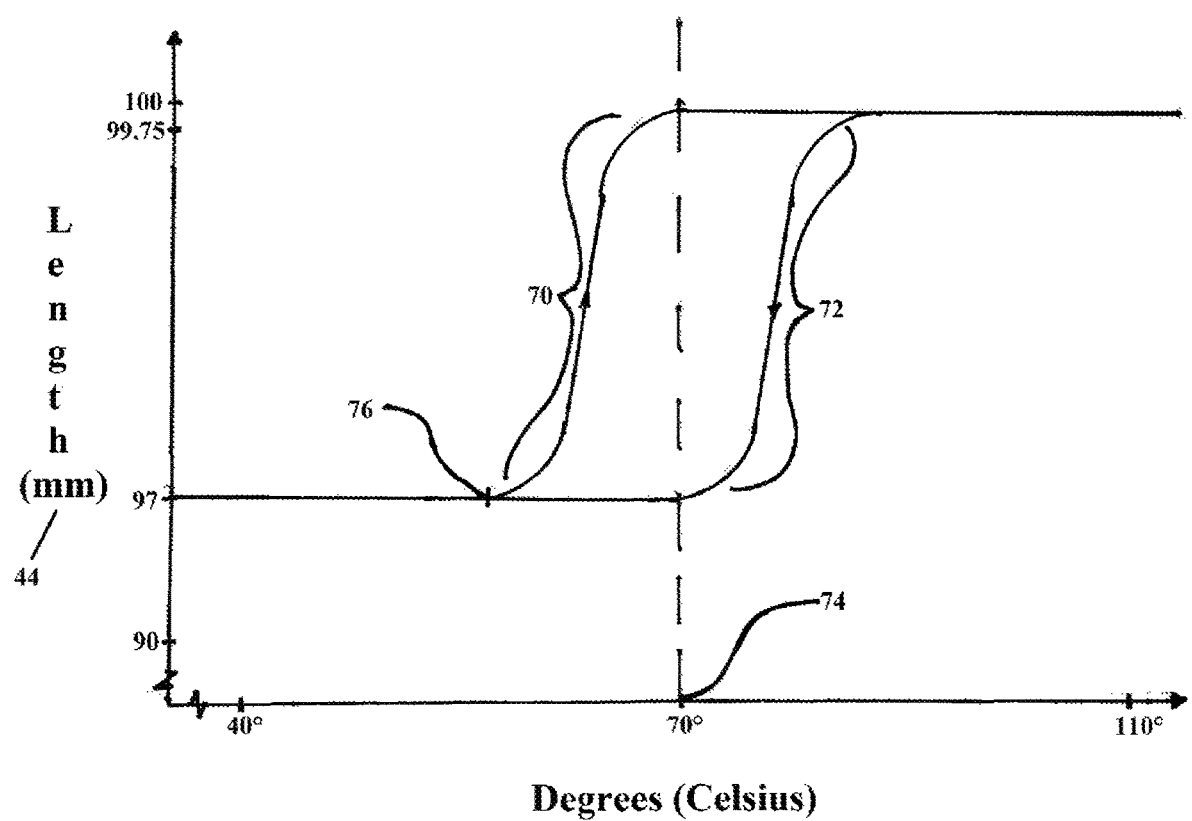
FIG. 5B depicts the heating, cooling and standby phases used by the dynamic compression garment using a different shape memory alloy of FIG. 5A.

FIG. 5B depicts the heating, cooling, and standby phases used by the compression garment apparatus using a different shape memory alloy of FIG. 5A.

The graph has an x-axis representing temperatures, wherein one of the temperatures is a target transition temperature 74 of a certain length of shape memory alloy. In this Figure, the target transition temperature 74 is shown as 70 degrees Celsius along the x-axis ranging from 40 degrees Celsius to 110 degrees Celsius.

The graph has a y-axis representing the length of the shape memory alloy, here the y-axis is drawn depicting a range from 90 mm to 100 mm with the length of the shape memory allow varying from 97 mm to 100 mm.

The graph shows a heating phase 70 causing a length 44 of the shape memory alloy upon reaching a target transition temperature 74 to either lengthen or shorten.

The graph shows a cooling phase 72 which causes a length 44 of the shape memory alloy at the target transition temperature 74 to either lengthen or shorten opposite to the length change caused by the heating phase.

The graph shows a standby phase 76 that maintains the temperature of the shape memory alloy just below the target transition temperature 74 keeping the length 44 of the shape memory alloy unchanged but preparing the shape memory alloy for the shortening or lengthening of the shape memory alloy.

Figure 6A:
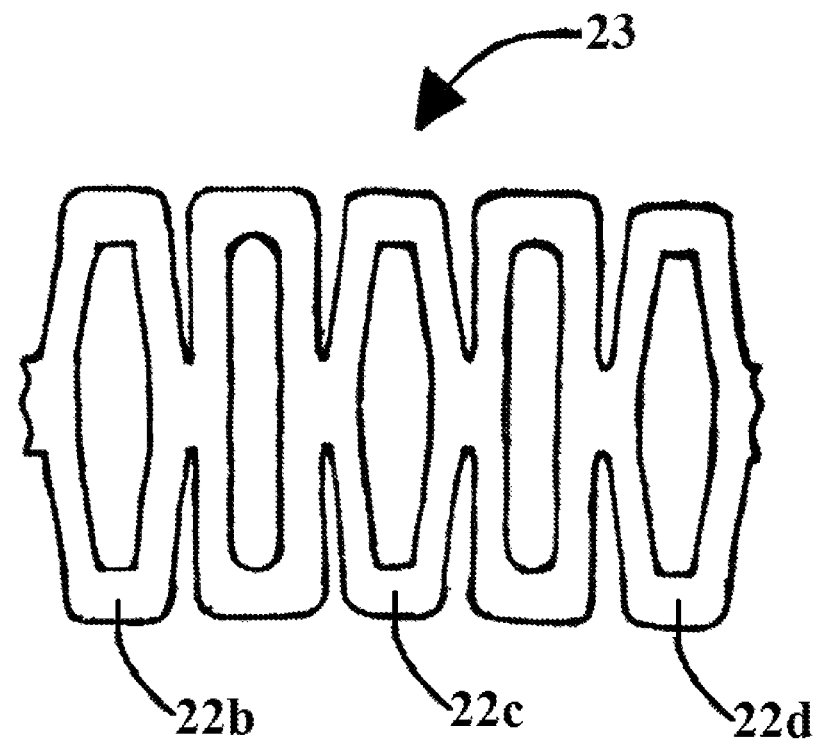
FIGS. 6A-6B show a spring link in an expanded shape and a contracted shape.

FIG. 6A shows three spring link 22a, 22b, and 22c. Each spring link is depicted in an expanded shape 23.

Figure 6B:
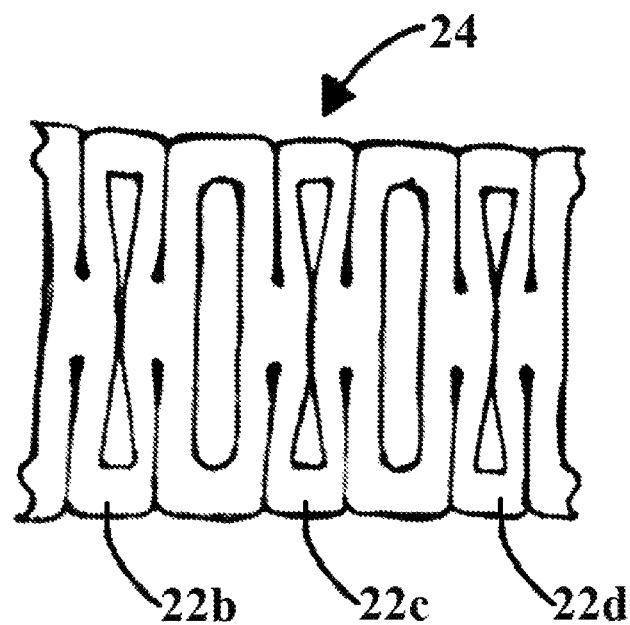

FIG. 6B shows three spring links 22a, 22b, and 22c. Each spring link is depicted in a contracted shape 24.

It can be seen in these Figures that the width of the spring link is presented to clarify that the width of the spring link expands to a more "donut-like" shape and contracts to an "I" shape when the shape memory alloy receives current. The order of the contraction and the expansion changes depending on which type of shape memory alloy is used, that is for some shape memory alloys, when current is applied, it causes the spring link to take on the contracted shape 24, while for different shape memory alloys when current is applied, the current causes the spring link to take on the expanded shape 23.

The spring link changes in shape when at least one occurs: (1) current is applied or released on the shape memory alloy and (2) pressure is applied by the tensioner to the shape memory alloy.

Figure 7A:
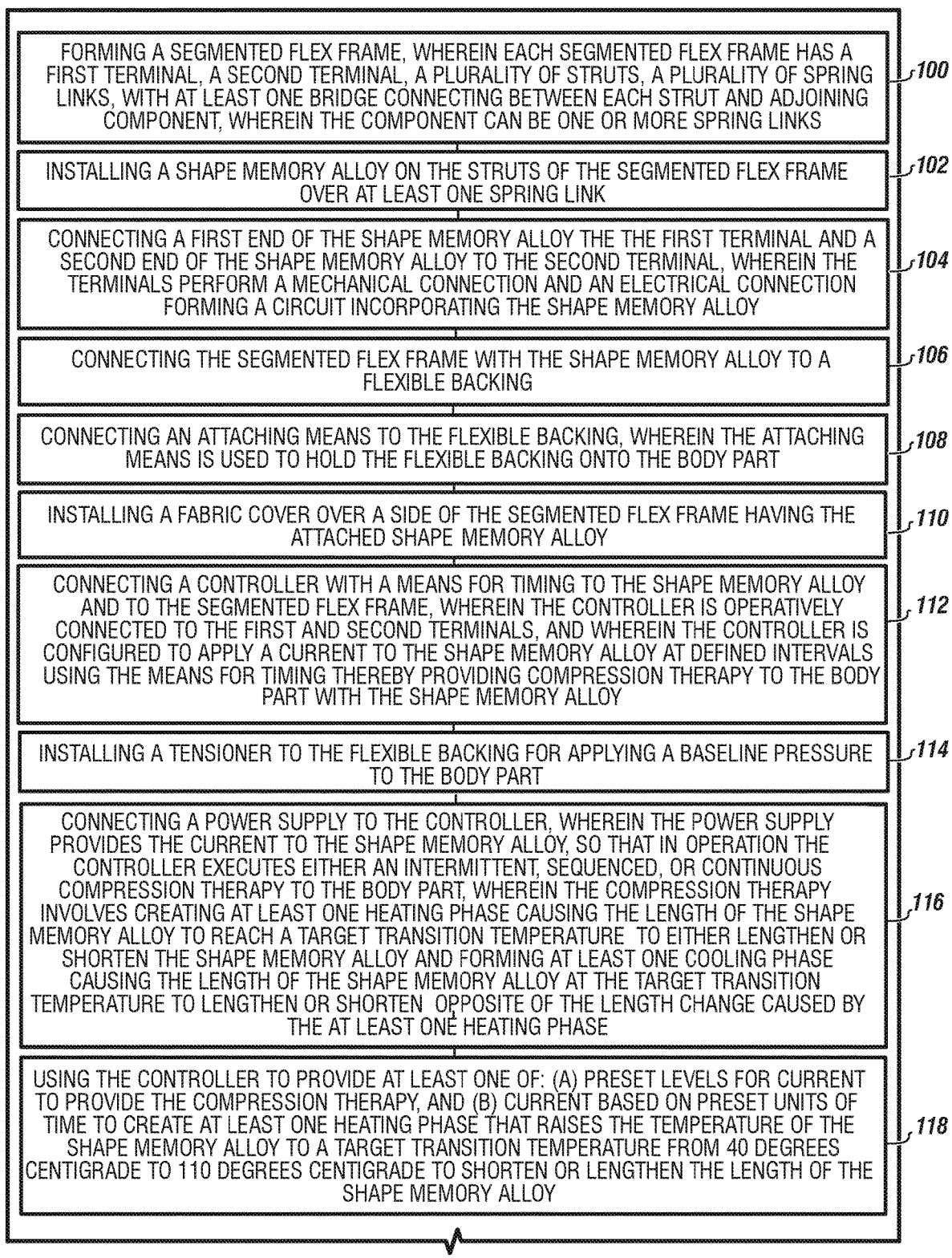

FIGS. 7A-7B provide a representation of the steps to build the dynamic compression garment according to the method.

The method to form a compression garment for a body part of a human or animal is depicted in this embodiment as steps The method can include forming a segmented flex frame, wherein each segmented flex frame has a first terminal, a second terminal, a plurality of struts, a plurality of spring links, with at least one bridge connecting between each strut and adjoining component, which can be one or more spring links, shown as step 100.

The method can include installing a shape memory alloy on the struts of the segmented flex frame over at least one spring link, shown as step 102.

The method can include connecting a first end of the shape memory alloy to the first terminal and a second end of the shape memory alloy to the second terminal, wherein the terminals perform a mechanical connection and an electrical connection forming a circuit incorporating the shape memory alloy, shown as step 104.

The method can include connecting the segmented flex frame with the shape memory alloy to a flexible backing, shown a step 106.

The method can include connecting an attaching means to the flexible backing, wherein the attaching means is used to hold the flexible backing onto the body part, shown as step 108.

The method can include installing a fabric cover over a side of the segmented flex frame having the attached shaped memory alloy, shown as step 110.

The method can include connecting a controller with a means for timing to the shape memory alloy and to the segmented flex frame, wherein the controller is operatively connected to the first and second terminals, and wherein the controller is configured to apply a current to the shape memory alloy at defined intervals using the means for timing thereby providing compression therapy to the body part with the shape memory alloy, shown as step 112.

The method can include installing a tensioner to the flexible backing for applying a baseline pressure to the body part, shown as step 114.

The method can include connecting a power supply to the controller, wherein the power supply provides the current to the shape memory alloy, so that in operation the controller executes either an intermittent, sequenced, or continuous compression therapy to the body part, wherein the compression therapy involves creating at least one heating phase causing a length of the shape memory alloy to reach a target transition temperature to either lengthen or shorten the shape memory alloy and forming at least one cooling phase causing the length of the shape memory alloy at the target transition temperature to lengthen or shorten opposite of the length change caused by the at least one heating phase, shown as step 116.

The method can include using the controller to provide at least one of: (a) preset levels for current to provide the compression therapy, and (b) current based on preset units of time to create at least one heating phase that raises the temperature of the shape memory alloy to a target transition temperature from 40 degrees Centigrade to 110 degrees Centigrade to shorten or lengthen the length of the shape memory alloy, shown as step 118.

The method can include using a sensor connected to the shape memory alloy or using the shape memory alloy itself, to measure at least one physical characteristic of the dynamic compression garment including changes in dimension of the compression garment apparatus, stiffness of the body part, changes in dimension of the body part; measurable physiological parameters of the human and/or animal such as heart rate, and blood pressure, and combinations thereof, shown as step 120.

The method can include creating at least one standby phase that maintains the temperature of the shape memory alloy just below the target transition temperature keeping the length of the shape memory alloy unchanged but preparing the shape memory alloy for the shortening or lengthening of the shape memory alloy, shown as step 122.

The method can include using the controller and computer instructions in the data storage to compare sensed real time measured garment dimensions to preset garment dimension values and change current delivery to the shape memory alloy to achieve the preset garment dimension values, shown as step 124.

An example of preset garment dimension values can be dimensions of the garments non-activated state, such as length of the segmented flex frame when not activated, and length of the segmented flex frame when initially tensioned, and length of the segmented flex frame when the shape memory alloy has initial current applied to the shape memory alloy and lengths when additional amounts of current are applied to the shape memory alloy.

The following examples aid in understanding the use of the garment formed according to the method.

An elderly person with very limited mobility and dementia is no longer able to take care of themselves. They require daily manipulation by a caregiver while they are in bed, to prevent bedsores and to maintain their tissues as well as possible. The garment would be placed by a caregiver onto an arm or leg to provide massage during their manual therapy.

One additional benefit of the invention is for diabetic patients because a very large percentage of advanced diabetics have peripheral neuropathy. Human feet have barely adequate blood flow, so they tend to heal less quickly that other parts of the body. As a result they are unable to feel sores developing on their feet and may easily develop foot ulcers, which then do not heal very well. Many diabetics loose one or both feet to diabetic ulcers, and sometimes they lose their life. This invention will enable diabetic people to treat their feet to daily massages to improve blood flow to both prevent and to help treat diabetic foot ulcers.

While these embodiments have been described with emphasis on the embodiments, it should be understood that within the scope of the appended claims, the embodiments might be practiced other than as specifically described herein.

What is claimed is:

1. A compression garment device, comprising:
at least one segmented flex frame;
a first terminal and a second terminal operably connected to the at least one segmented flex frame;
a shape memory alloy or a shape memory polymer disposed on the at least one segmented flex frame with a first end of the shape memory alloy or the shape memory polymer configured to engage the first terminal and a second end of the shape memory alloy or the shape memory polymer configured to engage the second terminal, the first terminal and the second terminal each configured to form a circuit incorporating the shape memory alloy or the shape memory polymer; and
a controller operatively connected to the first terminal and the second terminal, wherein the controller is configured to apply a current to the shape memory alloy or the shape memory polymer sufficient to shorten a dimension of the shape memory alloy or the shape memory polymer;
the at least one segmented flex frame comprising:
a series of frame segments including at least two struts and at least one spring link; wherein each of the struts is configured to receive the shape memory alloy or the shape memory polymer such that the shape memory alloy or the shape memory polymer is configured to decrease a distance between two adjacent struts;
wherein each of the at least one spring link is located entirely between a pair of adjacent struts of the at least two struts and configured to transition between a first shape and a second shape in response to a change of dimension of the shape memory alloy or the shape memory polymer; and
wherein each of the at least one spring link comprises at least two bridges, wherein each bridge is connected between an outer perimeter of the at least one spring link and an outer perimeter of an adjacent strut of the at least two struts of the pair of adjacent frame segments.

2. The compression garment device of claim 1, further comprising a fabric cover that is configured to be disposed over the shape memory alloy or the shape memory polymer and attached to the at least one segmented flex frame.

3. The compression garment device of claim 1, further comprising a tube of expandable fabric that is configured to be positioned over the at least one segmented flex frame.

4. The compression garment device of claim 1, further comprising a flexible backing and a tensioner secured to the flexible backing, the flexible backing configured to contact a body part of a user and the tensioner configured to apply a baseline pressure to the body part of the user.

5. The compression garment device of claim 1, wherein the shape memory alloy or the shape memory polymer is in a form selected from the group consisting of: a ribbon, a wire, a mesh, a sheet, a film, and combinations thereof.

6. The compression garment device of claim 1, wherein the controller comprises a microprocessor powered by a power supply, wherein the controller is in communication with a data storage, the data storage comprising computer instructions to instruct the microprocessor to:
provide preset levels of current to provide compression therapy; and
provide the current based on preset units of time.

7. The compression garment device of claim 6, further comprising a sensor configured to measure at least one physical characteristic of the compression garment apparatus selected from changes in dimension of the compression garment apparatus, and stiffness of a body part of a user.

8. The compression garment device of claim 6, further comprising a sensor operably connected to the controller configured for sensing and generating signals to the controller representing at least one of: changes in a dimension of the compression garment apparatus and stiffness of a body part of a user, changes in a dimension of the body part, measurable physiological parameters of the user, or combinations thereof.

9. The compression garment device of claim 1, further comprising a series of timers, wherein each timer of the series of timers is configured to provide current to the shape memory alloy or the shape memory polymer when the timer is on and no current to the shape memory alloy or the shape memory polymer when the timer is off, further wherein each timer of the series of timers is adapted to provide current to at least a portion of the shape memory alloy or the shape memory polymer on at least a portion of the at least one segmented flex frame.

10. The compression garment device of claim 1, further comprising at least one standby phase, wherein a temperature of the shape memory alloy or the shape memory polymer is held by the controller below a target transition temperature keeping the dimension of the shape memory alloy or the shape memory polymer unchanged but preparing the shape memory alloy or the shape memory polymer for changing the dimension of the shape memory alloy or the shape memory polymer.

11. The compression garment device of claim 6, the computer instructions in the data storage are further configured to instruct the microprocessor to compare sensed real time measured garment dimensions to preset garment dimension values and change current delivery to the shape memory alloy or the shape memory polymer to achieve the preset garment dimension values.

12. The compression garment device of claim 1, wherein the at least two struts, the at least one spring link located between the at least two struts, and the at least two bridges located between the at least two struts are all made from an identical material.

13. The compression garment device of claim 1, wherein the at least two struts, the at least one spring link located between the at least two struts, and the at least two bridges located between the at least two struts are all made during one injection molding process.

14. The compression garment device of claim 1, wherein:
a first bridge of the at least two bridges is located on a first side of the at least one spring link between the at least one spring link and a first strut of the at least two struts;
a second bridge of the at least two bridges is located on a second side of the at least one spring link between the at least one spring link and a second strut of the at least two struts; and
the at least one spring link has an inner perimeter in addition to the outer perimeter of the at least one spring link such that when the shape memory alloy or the shape memory polymer is used to decrease a distance between two adjacent struts of the at least two struts, the distance between the inner perimeter on the first side of the at least one spring link to the second side of the at least one spring link is decreased.

15. The compression garment device of claim 1, wherein a distance between an inner perimeter on a first side of the at least one spring link to the inner perimeter on a second side of the at least one spring link is reduced to zero as the inner perimeter on the first side of the at least one spring link contacts the inner perimeter on the second side of the at least one spring link.

16. A segmented flex frame, comprising:
a series of frame segments comprising at least two struts and at least one spring link;
wherein each of the at least two struts is configured to receive a portion of a shape memory alloy or a shape memory polymer such that a dimension of the shape memory alloy or the shape memory polymer is configured to decrease a distance between two adjacent struts of the at least two struts;
wherein each of the at least one spring link is located entirely between a pair of struts of the at least two struts and is configured to transition between a first shape and a second shape in response to a reduction of the dimension of the shape memory alloy or the shape memory polymer; and
wherein each of the at least one spring link comprises at least two bridges, wherein each bridge of the at least two bridges is connected between an outer perimeter of the at least one spring link and an outer perimeter of an adjacent strut of the at least two struts.

17. The segmented flex frame of claim 16, wherein the segmented flex frame is configured to connect to a flexible backing for contacting a body part of a user.

18. The segmented flex frame of claim 16, further comprising:
a first terminal and a second terminal operably connected to the segmented flex frame;
the shape memory alloy or the shape memory polymer disposed on the segmented flex frame with a first end of the shape memory alloy or the shape memory polymer configured to engage the first terminal and a second end of the shape memory alloy or the shape memory polymer configured to engage the second terminal; and a controller operatively connected to the first terminal and the second terminal, wherein the controller is configured to apply a current to the shape memory alloy or the shape memory polymer sufficient for the reduction of the dimension of the shape memory alloy or the shape memory polymer.

19. The segmented flex frame of claim 16, wherein the at least two struts, at least one of the at least one spring link located between the at least two struts, and the at least two bridges located between the at least two struts share a common planar face.

20. The segmented flex frame of claim 16, wherein the segmented flex frame is one integral piece created with an injection molding process.

\* \* \* \* \*